Figure 3:
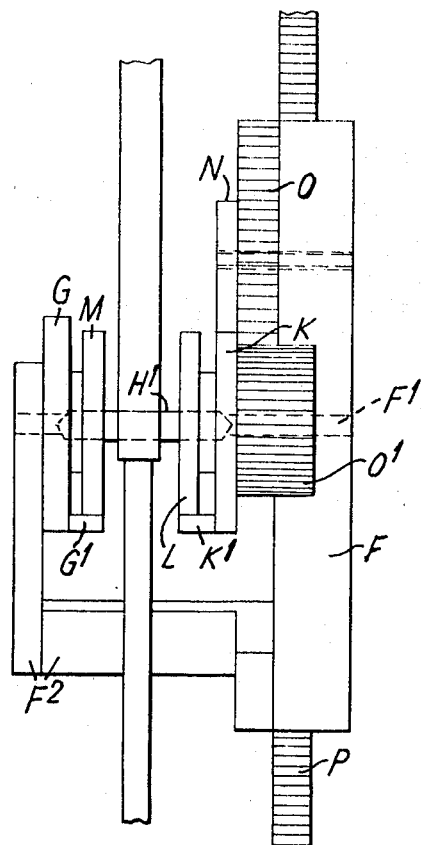

United States Patent [19]
Perkins et al.

[11] 3,952,585
[45] Apr. 27, 1976

[54] APPLANATION TONOMETERS

[76] Inventors: Edward Sylvester Perkins, 16 Loom Lane, Radlett, Hertford; Henry James Stockwell, Cymru, Epping Road, Roydon, Essex, both of England

[22] Filed: June 30, 1971

[21] Appl. No.: 158,508

[30] Foreign Application Priority Data
July 1, 1970 United Kingdom............ 32010/70

[52] U.S. Cl. .................................................. 73/80
[51] Int. Cl.²............................................ A61B 3/16
[58] Field of Search ........... 73/80, 81, 84, 94, 95.5, 73/139, 141 AB, 160; 177/170, 227

[56] References Cited
UNITED STATES PATENTS

| | | | |
|---|---|---|---|
| 3,247,596 | 4/1966 | Hintermaier................. | 73/94 X |
| 3,446,061 | 5/1969 | Draeger et al................ | 73/80 |
| 3,647,010 | 3/1972 | Beardmore et al............ | 177/170 X |

*Primary Examiner*—James J. Gill
*Assistant Examiner*—Anthony V. Ciarlante
*Attorney, Agent, or Firm*—Brisebois & Kruger

[57] ABSTRACT

This invention relates to an applanation tonometer for measuring a patient's intraocular pressure by applying an applanating pressure to the cornea of the patient's eye to produce a flattened area of predetermined size thereon, such applanating pressure being determined conjointly by an adjustable main spring and at least one compensating spring, the characteristics of the compensating spring being such that the total applanating pressure will bear an approximately linear relationship to an indicating movement dependent on the adjustment of the main spring. Preferably, the adjustment of the main spring is effected by control means operative to adjust the anchorage of such spring, the control means also acting to effect movement of an indicating member for indicating the said applanating pressure.

4 Claims, 8 Drawing Figures

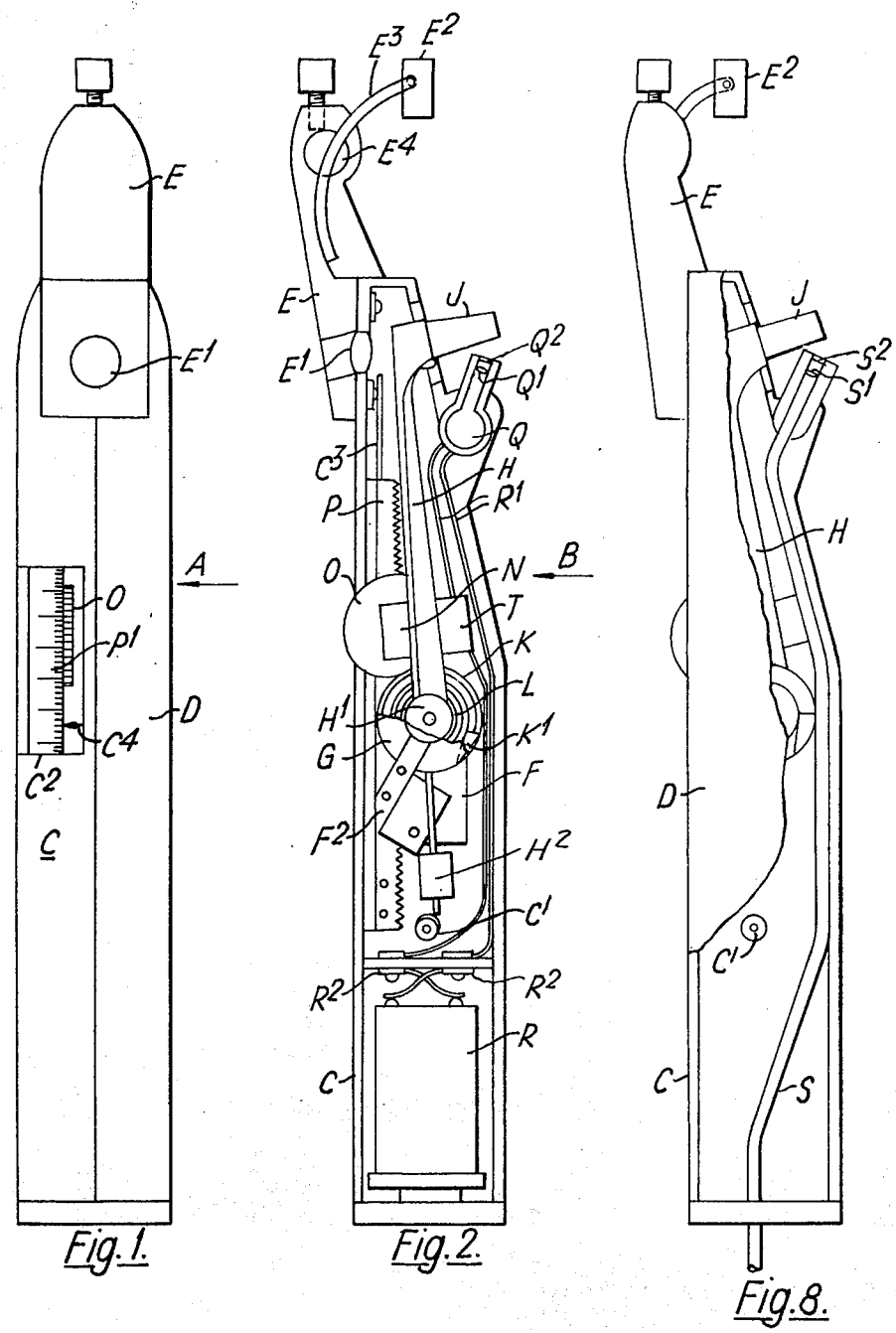

APPLANATION TONOMETERS

In certain eye diseases, notably glaucoma, one of the symptoms is an increase in the intraocular pressure. An instrument for measuring the intraocular pressure or for indicating variations thereof is termed a "tonometer". Various types of tonometer have been used, but one especially desirable type is that known as an applanation tonometer, in which a plane surface is pressed against the cornea of the eye to produce a flattened area thereof. Such flattened area will be circular or nearly circular in the case of a spherical cornea, but may be non-circular in the case of a eye with a sight defect. There is a known relationship between the pressure applied to the cornea, the diameter (or equivalent diameter) of the flattened area, and the intra-ocular pressure, and in one simple arrangement the applied pressure is gradually increased until it produces a flattened area of a chosen standard diameter (or equivalent diameter), so that the applied pressure then bears a definite relationship to the intraocular pressure and can be taken as a measure thereof.

British Pat. Specification No.862920 describes an applanation tonometer of this kind and mentions two factors which can produce errors in this method of measurement, namely the rigidity of the cornea and the adhesion of the applanating plane surface to the eye due to the presence of lachrymal fluid. These two factors however cause errors in opposing senses, and it has been found that provided the standard flattened area is chosen to lie within predetermined limits (between 2.7 and 4 millimeters in diameter), these two errors will substantially cancel each other out, so that a sufficiently accurate measure of the intraocular pressure can be obtained.

In this prior known arrangement, the applanating plane surface is formed on a block of transparent material, so that the diameter of the flattened area can be checked by observation through such block, and in a preferred arrangement this block carries a split field device, for example two prisms causing opposite deflections of two halves of the field, so that the attainment of the chosen standard diameter can be determined by a relative lateral displacement of the two semi-circles (representing the two halves of the boundary of the flattened area) by an amount equal to the diameter of the flattened area, so that the boundary of the flattened area will appear in a form resembling a letter S.

The applied pressure may be derived from a spring, preferably acting on the block carrying the applanating plane surface through a pivoted lever, and the gradual increase in the applied pressure may be brought about by gradual adjustment of the "fixed" anchorage of such spring.

The present invention has for its object to provide an improved applanation tonometer of this general type. In particular an especially important object of the invention is to provide an arrangement, in which the graduation of the scale indicating the applanating pressure applied to the cornea shall be linear or nearly linear. It is also desirably that any necessary recalibration of the instrument or zero adjustment thereof can be readily and easily effected without dismantling the instrument. Other desirable features are that the moving system of the instrument shall have low inertia, and that the movement of the applanating plane surface from its normal rest position to its operative applanating position applying pressure to the patient's eye shall be kept small in order to minimise the difference in the force applied to the moving system in such two positions.

In the applanation tonometer according to the present invention, the applanating pressure applied to the cornea of the patient's eye to produce a flattened area of predetermined size thereon is derived from or controlled by an adjustable main spring in conjunction with at least one compensating spring so arranged that the applanating pressure will bear an approximately linear relationship to an indicating movement dependent on the adjustment of the main spring.

The adjustment of the main spring is preferably effected by control means operative to adjust the anchorage of such spring, the control means also acting to effect movement of a member for indicating the said applanating pressure. Thus, the tonometer may conveniently comprise a pivot member carrying an arm through which the applanating pressure is applied to the patient's eye, a main spring and a compensating spring each anchored at one end to such pivot member, means for anchoring the free end of the compensating spring to the framework of the tonometer, an anchorage member for the free end of the main spring mounted for rotational movement about the axis of the pivot member, control means for effecting rotational adjustment of such anchorage member and thereby also of the pivot member, and an indicating member actuated by the control means for giving an indication of the said applanating pressure.

The moving system of the tonometer is preferably so mounted and balanced that the resultant indication is independent of the orientation of the tonometer relatively to gravitational force. This is advantageous since, in contrast with most of the prior known tonometers, it permits the tonometer to be used satisfactorily, whether the patient is in a sitting or recumbent or other position.

The applanation tonometer according to the invention preferably also includes means for illuminating the flattened area of the patient's eye, together with switching means for automatically cutting off such illumination when the moving system of the tonometer is in or adjacent to its normal rest position. Such illuminating means may conveniently be energised from a battery or other source of power housed in the framework of the tonometer. In an alternative arrangement, the tonometer may include a flexible tube or bundle of flexible tubes through which light from a suitable source is transmitted for illuminating the flattened area of the patient's eye.

The applanating pressure is preferably applied to the cornea of the patient's eye by a plane surface on a block of transparent material, so that the flattened area on the cornea can be observed through such block. The block conveniently incorporates a split field device for laterally displacing two halves of the image of the flattened area in opposite directions to produce a total relative displacement equal to the diameter or effective diameter of the boundary of the flattened area.

The invention may be carried into practice in various ways, but a preferred construction of applanation tonometer in accordance therewith is illustrated by way of example in the accompanying drawings.

In this preferred construction, the tonometer is in the form of a light portable instrument housed in a casing formed of two elongated interfitting parts, of suitable material, such for example as fibre glass. For convenience of description, one of such two parts will be referred to as the base and the other as the cover, irrespective of the fact that in practical use the tonometer may be held in any orientation suited to the comfort and convenience of the patient and of the doctor or other person using the instrument. For a like reason, it will be assumed in the following description that the patient and the doctor are seated facing one another, with the tonometer held vertically in the doctor's hand, so that the end hereinafter referred to as the "upper" end is located between the patient's eye and the doctor's eye, the "front" of the tonometer being assumed to be the side thereof nearer to the patient.

Figure 4:
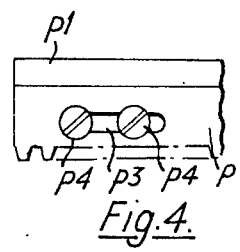
Figure 5:
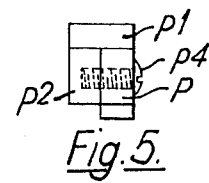
Figure 6:
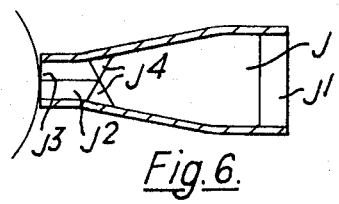
Figure 7:
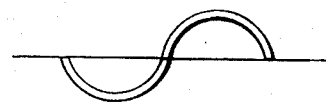

In the accompanying drawings,

FIG. 1 shows the tonometer in elevation viewed from behind,

FIG. 2 shows the main moving parts of the tonometer mounted in the base, viewed in the direction of the arrow A in FIG. 1, FIG. 3 shows on a larger scale the middle portion of the said moving parts, viewed in the direction of the arrow B in FIG. 2, FIGS. 4 and 5 illustrate in two views at right angles to one another a convenient method of securing together the two portions of a sliding rack bearing the indicating scale of the instrument, FIG. 6 shows a convenient mounting for the above-mentioned block of transparent material, which in use of the instrument is pressed against the cornea of the patient's eye, FIG. 7 illustrates the view seen by the doctor or other practitioner using the instrument when such block of transparent material has been applied to the cornea with correct flattening pressure, and FIG. 8 illustrates a modified construction of tonometer viewed in the same direction as FIG. 2.

In the preferred construction shown in FIGS. 1–7, the base C and the cover D are each of trough-like form with their side edges shaped to interfit closely with one another. To secure these two parts firmly together, one of the two parts (as shown, the base C) carries a post $C^1$ into which a screw passing through a hole in the other part can be tightened.

The main moving parts of the instrument are housed in the base C, whilst either the base C or the cover D (as illustrated the base C) carries at its upper end a fitting E incorporating an inspection eyepiece $E^1$ and a member $E^2$ for resting against the patient's forehead. Such headrest member $E^2$ is loosely carried on a forwardly extending arm $E^3$, which can be adjusted about a horizontal pivot $E^4$ into the most comfortable position and can be securely clamped in such position.

The base C has firmly secured to it at a convenient intermediate position in its length a bed plate F from which projects a bearing member $F^1$ and also a bracket $F^2$ fixedly carrying an anchor plate G parallel to and spaced from the bed plate F. The bearing member $F^1$ and such fixed anchor plate G carry bearings for a pivot member $H^1$ carrying a lever H, one arm of which extends to the upper end of the base C, where it carries an applanating member J adjacent to the inspection eyepiece $E^1$ mounted in the fitting E. The other arm of this lever H extends downwardly for a short distance from the pivot member $H^1$ and carries a counterweight $H^2$, such that the two arms of the lever including the parts carried thereby are well balanced against one another.

The total weight of the lever H and pivot member $H^1$ is kept as small as possible, consistent with maintaining adequate rigidity of the lever arms. The bearing member $F^1$ projecting from the bed plate F also supports a second anchor plate K which can rotate about the same axis as the pivot member $H^1$, but independently thereof, the lever being movable in a plane substantially midway between the two anchor plates G and K.

A main spring L, which may conveniently be in the form of a flat spiral, is anchored at its inner and end to the pivot member $H^1$ and at its outer end to a projection $K^1$ from the rotatable anchor plate K. A compensating spring M, likewise in the form of a flat spiral, is anchored at its inner end to the pivot member $H^1$ and at its outer end to a projection $G^1$ the fixed anchor plate G. The two springs L and M thus lie one on either side of the lever H, but with adequate clearance therefrom.

Another part of the bed-plate F carries a second bracket N, such bracket N and the bed-plate F carrying bearings for a toothed finger wheel O, a small portion of which projects through a slot $C^2$ in one side wall of the base C, so that it can be rotated by the doctor's finger. This finger wheel O also meshes with a part of the teeth of a relatively thick gear wheel $O^1$ secured to the rotatable anchor plate K on the face thereof remote from the main spring L. SUch gear wheel $O^1$ is thick enough for its teeth also to mesh with the teeth of a long rack P, which is mounted to slide past the finger wheel O, with adequate clearance therefrom, in a groove formed between the side wall of the base C and a rib $O^3$ upstanding from the base. The rack P is trapped in such groove by an overlapping portion of the bracket $F^2$ carrying the fixed anchor plate G, thereby ensuring the clearance from the finger wheel. Such rack P carried a graduated scale $P^1$, which is exposed to view through the opening $C^2$ cut in the side wall of the base C and cooperates with an index mark $C^4$ on the outer surface of such side wall.

The finger wheel O is of considerably larger diameter than the gear wheel $O^1$ with which it meshes, so that a relatively small angular movement of the finger wheel O will cause a much larger angular movement of the gear wheel $O^1$, and the maximum movement of the finger wheel is limited to less than one complete revolution, during which the whole of the graduated scale on the rack P passes the fixed index mark $C^4$.

The rack P is secured to a projection $P^2$ from the graduated scale $P^1$ by a pair of clamping screws $P^4$ (see FIGS. 4 and 5) passing through a slot $P^3$ in the scale. Such slot $P^3$ is made longer than is necessary to accomodate the two clamping screws $P^4$, thus permitting an initial adjustment of the zero of the scale $P^1$ relatively to the rack P to ensure accurate positioning of the scale on the rack.

The applanating member J carried at the upper end of the long lever arm H may be arranged in various ways, but is made of transparent material so that the size of the flattened area of the patient's cornea can be viewed through the inspection eyepiece and through the applanating member. In one especially convenient arrangement the applanating member is arranged in the manner described in the above-mentioned British Patent No.862920. In this arrangement (see FIG. 6) the applanating member J is mounted in the narrow front end of a small conical housing. The broader rear end of such housing is closed by a transparent plate-like member $J^1$.

The applanating member J comprises a block J² of transparent material having a plane front face J³, which in use of the instrument is pressed against the cornea of the patient's eye. The rear end of the block J² is formed to provide two opposing prisms J⁴ which split the field of views into two equal halves so that the two halves of the image of the flattened area of the cornea are laterally displaced in opposite directions by an amount equal to the diameter of the predetermined size of flattened area, whereby the image of the boundary of the flattened area appears as two semi-circles relatively displaced in the direction of their common diameter to a position in which they make up a form somewhat resembling a letter S as indicated in FIG. 7. In some cases of patients with an eye defect, the boundary of the flattened area may not be a true circle, but will be somewhat non-circular, but it is still practicable to recognise a size of flattened area which is the equivalent to the predetermined size of circular flattened area obtained with eyes of normal vision.

In order to be able to observe the boundary of the flattened area sufficiently clearly, it is desirable to provide means for illuminating the cornea of the patient's eye. In one simple arrangement, this is achieved by the provision on the base C of a mounting for a small electric light bulb, tipped with a lens Q¹ and a suitable light filter Q². The unit comprising the lampbulb, the lens and the filter is mounted to be angularly adjustable into the best position for illumination. Such light bulb can be energised through wires R¹ passing down through the base C to terminals R², which may be energised by a small battery R housed in a compartment at the bottom end of the base C. Such battery may be replaced, if desired, by a transformer energised through a trailing cable from a mains supply. In another alternative, shown in FIG. 8, the cornea may be illuminated by light from a suitable source transmitted through a bundle of such flexible tubes S, provided with a lens S¹ and ultraviolet filter S² at the outlet end for concentrating the light on the cornea.

It is convenient to provide means for automatically controlling the illuminating means. This may be achieved by means of a microswitch T disposed adjacent to the surface of the finger wheel, so that it can be operated by the rotation of the finger wheel O. Thus, it is desired to switch off the light when the rack P is in its zero position and to switch the light on when the rack moves away from its zero position. In one arrangement the actuating member of the microswitch T is spring urged against the surface of the finger wheel O, such surface being provided in the zero position with a shaped recess, so that in such zero position the actuating member holds the switch in its open position, the switch automatically closing as soon as the finger wheel O is moved away from the zero position.

The operation of the tonometer will now be described, starting with the moving system in its normal rest position, at or closely adjacent to the zero position. The doctor positions the instrument with the head rest E² against the patient's forehead and the eyepiece E¹ in the correct position for viewing the patient's cornea. He then moves the finger wheel O away from the zero position, thus switching on the light and causing the rotatable anchor plate K slowly to rotate to wind up the main spring L and thus to cause such spring to apply a force to the pivot member H¹ to begin to move the lever H and thereby to move the applanating member J forward into contact with the patient's cornea and to apply a flattening pressure thereto. He continues to rotate the finger wheel O until, by his observation through the eye-piece E¹ and the applanating member J, he sees that the boundary of the flattened area has grown to the predetermined standard diameter. He then observes the reading on the rack scale P¹, to show how far the rack has moved from its zero position to reach the operative position, such reading being a measure of the intraocular pressure in the patient's eye.

It is important that the initial movement of the applanating member J from its normal rest position into the position in which it makes operative contact with the cornea should be extremely small, in order to avoid any significant change in the force applied by the main spring L on the applanating member between such two positions.

If the main spring L alone were relied upon to provide the pressure of the applanating member on the cornea, the relationship between such pressure and the movement of the rack P might not give the desired linear relationship. The function of the compensating spring M is to modify the total spring force exerted on the pivot member H¹, so as to achieve the desired linear relationship. Thus, during operation of the instrument the compensating spring M adds to or subtracts from the force exerted by the main spring L a further force due to the compensating spring. It has been found possible, by operating the tonometer against accurately known resistive forces of the appropriate magnitude, to provide a compensating spring with such characteristics in relation to those of a chosen main spring that, a close approximation to a linear relationship between the rack movement and the pressure applied to the cornea due to the resultant of the spring forces on the pivot member can be achieved. In some instances, it may be found preferable to use a combination of two compensating springs having different characteristics in order to provide the desired modification of the main spring force.

It will be appreciated that the mounting of the moving system in the foregoing arrangement is such that it is fully balanced independently of gravitational forces, and can thus be satisfactorily operated in any orientation, for example with the patient in a recumbent position, instead of in a seated position. Further, the fact that the scale is linear, makes it possible to effect recalibration of the instrument (for example following replacement of some part) without replacement of the scale.

What we claim as our invention and desire to secure by Letters Patent is:

1. An applanation tonometer for measuring the intraocular pressure of a patient's eye by applying an applanating pressure to the cornea and measuring the amount of pressure needed to produce a flattened area of predetermined size thereon, comprising an applanating member for engaging with the cornea, a lever arm carrying such member, and mounted to pivot about an axis, a pivot member which is mounted on such axis and from which the lever arm extends, means for applying a turning force to such pivot member for causing pressure to be exerted on the cornea, such force applying means including an adjustable main spiral spring surrounding the said axis, control means for effecting adjustment of the main spring, means for anchoring the inner end of the main spring to the pivot member, and an anchorage member for the outer end of the main spring mounted for rotational movement about the said axis in accordance with the operation of the control means, such rotational movement causing rotation of the pivot member and thereby causing the applanating pressure to be applied to the cornea, an indicating member actuated by the control means for giving an indication of the applanating pressure applied to the cornea, and at least one compensating spiral spring surrounding the said axis, means for anchoring the inner end of the compensating spring to the pivot member and means for anchoring the outer end of the compensating spring to the casing of the tonometer, the characteristics of the compensating spring being such in relation to those of the main spring that the total applanating pressure will bear an approximately linear relationship to the movement of the indicating member.

2. An applanation tonometer as claimed in claim 1 including an electric lamp arranged to illuminate the flattened area of the cornea of the patient's eye, a battery or other source of power for energising the lamp, and a switch actuated by movement of the control means to connect the source of power to the lamp when the control member is operated to move the indicating member away from its zero position.

3. An applanation tonometer as claimed in claim 1 including means for illuminating the flattened area of the cornea of the patient's eye, said means comprising a lens mounted on the tonometer adjacent the applanating member, an electric lamp, a source of power, and light transmitting means comprising a flexible rod or bundle of rods connecting the lamp with the lens.

4. An applanation tonometer as claimed in claim 1, in which the moving system of the tonometer is balanced, whereby the resultant indication is independent of the orientation of the tonometer relatively to gravitational force.

* * * * *